(12) United States Patent
Willis et al.

(10) Patent No.: US 7,101,477 B1
(45) Date of Patent: Sep. 5, 2006

(54) LIQUID CHROMATOGRAPHY COLUMN HAVING METAL TO METAL SEALS

(75) Inventors: Frank M. Willis, Deptford, NJ (US); Clyde L. Machamer, Elkton, MD (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/224,778

(22) Filed: Sep. 13, 2005

(51) Int. Cl.
*B01D 15/08* (2006.01)

(52) U.S. Cl. .................... 210/198.2; 210/656
(58) Field of Classification Search ............. 210/635, 210/656, 198.2; 96/101, 106; 422/70
See application file for complete search history.

(56) References Cited

U.S. PATENT DOCUMENTS

| | | | |
|---|---|---|---|
| 4,026,803 A | | 5/1977 | Abrahams et al. |
| 4,313,828 A | | 2/1982 | Brownlee |
| RE31,974 E | * | 8/1985 | Brownlee .............. 210/198.2 |
| 5,238,556 A | * | 8/1993 | Shirkhan ............... 210/198.2 |
| 5,938,919 A | * | 8/1999 | Najafabadi ............ 210/198.2 |
| 6,095,572 A | * | 8/2000 | Ford et al. ............... 285/361 |
| 6,193,286 B1 | * | 2/2001 | Jones et al. ............. 285/354 |
| 6,387,256 B1 | | 5/2002 | Tuvim |
| 6,527,951 B1 | | 3/2003 | Tuvim |
| 6,679,989 B1 | | 1/2004 | Willis et al. |

FOREIGN PATENT DOCUMENTS

WO   WO 2004/024285 A1   3/2004

* cited by examiner

*Primary Examiner*—Ernest G. Therkorn

(57) ABSTRACT

A column for liquid chromatography includes a chamber adapted to receive packing medium. Openings in the chamber allow fluid to pass through it. Porous plugs in the chamber retain the packing medium. A fitting has a contact surface that engages a landing area on the chamber surrounding one of the openings. Engagement of the contact surface with the landing area forms a metal to metal seal between the fitting and the chamber. A method of sealing a column for liquid chromatography is also disclosed. The method involves a chamber containing packing medium, the chamber having an opening surrounded by a landing area. The method includes providing a compression fitting having a contact surface and compressing the contact surface against the landing area to form a fluid tight seal between the compression fitting and the chamber.

21 Claims, 2 Drawing Sheets

LIQUID CHROMATOGRAPHY COLUMN HAVING METAL TO METAL SEALS

BACKGROUND OF THE INVENTION

High performance liquid chromatography (HPLC) is a process by which one or more compounds from a chemical mixture may be separated and identified. A transport liquid, for example a solvent, is pumped under high pressure through a column of packing medium, and a sample of the chemical mixture to be analyzed is injected into the column. As the sample passes through the column with the liquid, the different compounds, each one having a different affinity for the packing medium, move through the column at different speeds. Those compounds having greater affinity for the packing material move more slowly through the column than those having less affinity, and this speed differential results in the compounds being separated from one another as they pass through the column.

The transport liquid with the separated compounds exits the column and passes through a detector, which identifies the molecules, for example by spectrophotometric absorbance measurements. A two dimensional plot of the detector measurements against elution time or volume, known as a chromatogram, may be made, and from the chromatogram the compounds may be identified.

For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, are undesirable as they may allow minor components of the mixture to be masked by major components and go unidentified.

Columns for HPLC typically comprise high strength stainless steel tubes packed under high pressure with packing media comprising, for example, silane derivatized silica spheres having a diameter less than 20 microns. The packing media is held within the tube by sintered stainless steel frits. The frits are porous and allow the transport liquid and the sample to pass through the tube. It is advantageous to press the frits into the bore of the tube with an interference fit to prevent the packing material from escaping past the frits. Threaded end fittings are positioned at opposite ends of the tube. The end fittings keep the frits within the bore, compress the packing media to help maintain its hydraulic orientation, and are adapted to receive standard fittings from capillary tubes for connecting the column to a chromatograph.

Dead space within a column should be avoided because it allows mixing of the transport liquid and the sample that degrades the column performance. This manifests itself as a broadening of the peaks and a concomitant decrease the resolving capability of the HPLC apparatus.

SUMMARY OF THE INVENTION

The invention concerns a column for liquid chromatography. The column is adapted to contain a packing medium. The column comprises a chamber for receiving the packing medium. An opening is positioned in the chamber allowing liquid to pass through it. A porous plug blocks the opening and retains the packing medium within the chamber. A landing area surrounds the opening. A compression fitting has a contact surface that is engageable with the landing area. A duct extends through the compression fitting in fluid communication with the opening. The compression fitting is adjustably movable to force the contact surface against the landing area thereby deforming either the landing area or the contact surface to form a fluid tight seal between the compression fitting and the chamber.

The invention also includes a method of sealing a column for liquid chromatography, the column comprising a chamber containing packing medium, the chamber having an opening surrounded by a landing area, the method comprising:

(A) providing a compression fitting having a contact surface;

(B) compressing the contact surface against the landing area to deform either the contact surface or the landing area and thereby form a fluid tight seal between the compression fitting and the chamber.

DETAILED DESCRIPTION

Figures 1, 1A:
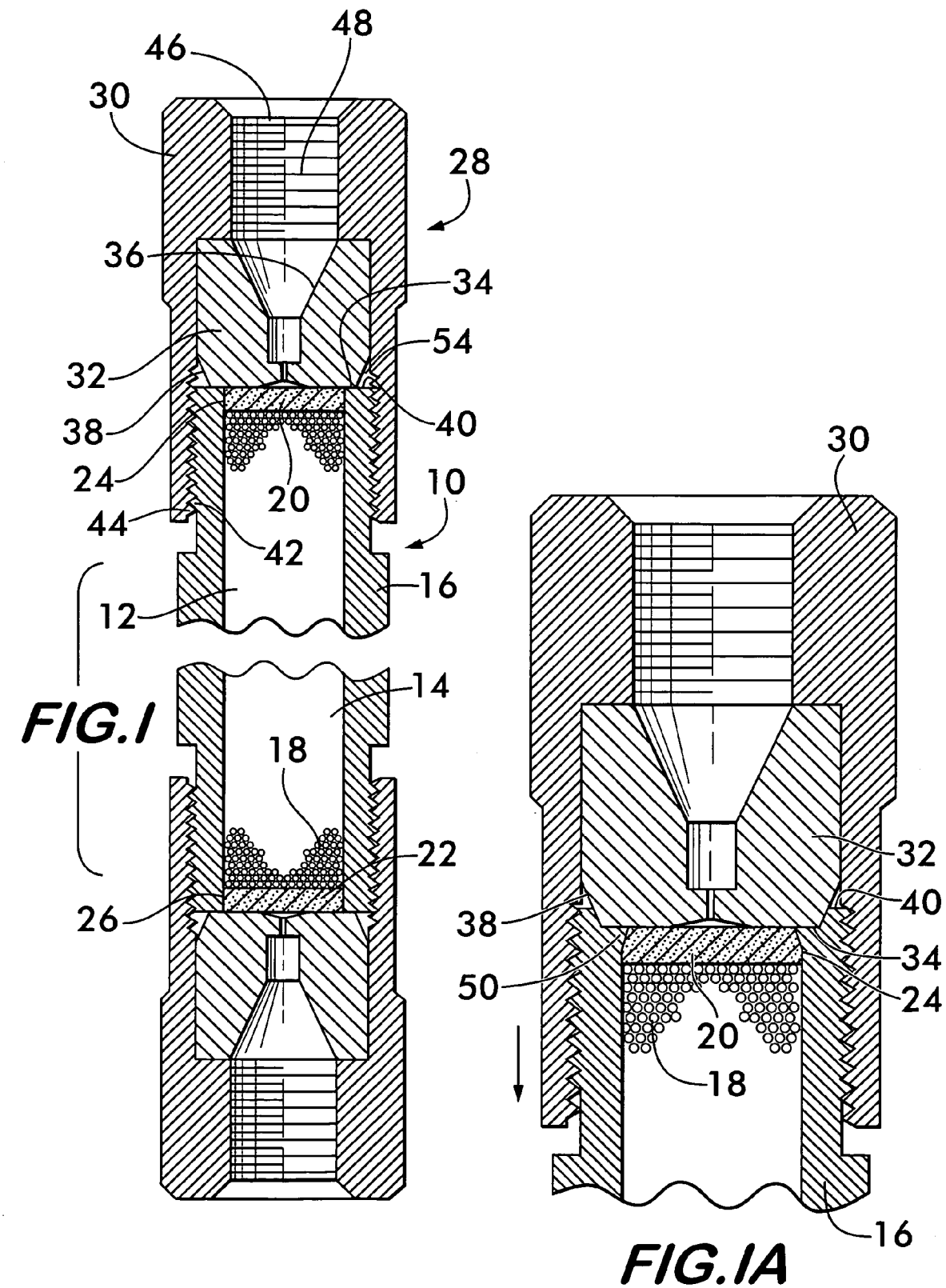
FIG. 1 is a longitudinal sectional view of a column for liquid chromatography according to the invention.
FIG. 1A is a sectional view of a portion of the column shown in FIG. 1 on an enlarged scale.

FIG. 1 shows a liquid chromatography column 10 according to the invention. Column 10 may be any type of column used in liquid chromatography, examples of which include an analytical column, a preparatory column and a guard column. The columns may have outer diameters that range between about 0.25 inches and about 1.125 inches and lengths up to about 10 inches.

Column 10 comprises a chamber 12, preferably defined by the bore 14 of a tube 16. Bore 14 contains a packing medium 18 used in liquid chromatography analysis, for example, silane derivatized silica spheres having a diameter of less than 20 microns. The packing medium is packed under high pressure and is retained within bore 14 by porous metal plugs 20 and 22 that are inserted into the bore at openings 24 and 26 in opposite ends of tube 16. The plugs are inserted and compress the packing material to reestablish some of the pressure lost after the packing process when the pressure is removed to complete assembly of the column. Plugs 20 and 22 are preferably sintered stainless steel frits that are pressed into bore 14 in an interference fit typically between 0.002 and 0.006 inches depending on the size of the column and the operating pressure. The interference fit allows the plugs to seal against the inner surface of tube 16 and prevent leakage of the packing medium from bore 14. The interference fit of the plugs eliminates the need for additional seals which would increase the cost of the column and decrease its performance by causing dead space that would promote mixing of the transport liquid.

At least one compression fitting 28 is positioned at an end of tube 16. Compression fitting 28 preferably comprises a threaded nut 30 and a compression body 32 that has a contact surface 34 at one end that engages tube 16. Compression fitting 28 has a duct 46 passing therethrough that is in fluid communication with bore 14 though one of the aforementioned end openings 24. In the embodiment shown in FIG. 1, the contact surface 34 is defined by a chamfer 38 at the end of the compression body 32. Chamfer 38 reduces the area of contact surface 34 for reasons explained below.

Opening 24 is surrounded by a landing area 40 at the end of tube 16. Landing area 40 preferably takes the form of an annular surface surrounding the bore 14 and receives the contact surface 34 of the compression body 32. The threaded nut 30 is mounted on tube 16 and engages the compression body 32 to retain it to the tube. Nut 30 preferably has internal screw threads 42 that engage complementary outer screw threads 44 on the tube thereby rendering the compression fitting adjustably movable. The compression fitting 28 including both the nut 30 and the compression body 32 are adapted to connect the column 10 to a capillary tube (not shown) for use of the column in a liquid chromatograph. To that end, the duct 46 passing through the compression fitting 28 has internal screw threads 48, and a tapered section 36 to receive standard fittings for connection to the liquid chromatograph.

Upon tightening of compression fitting 28, the contact surface 34 is forced against the landing area 40 of tube 16 and a metal to metal seal is formed between them. The seal is effected by tightening the compression fitting so that either the contact surface 34 or the landing area 40 deform plastically beyond the yield point of the material from which they are formed. The deformation will produce a fluid tight seal adequate for the relatively high pressures at which modern high performance chromatographs operate without the need for additional sealing members such as O-rings or extrusion type seals. It is advantageous to avoid such additional elements as they add to the cost of the column and degrade its performance because they create voids in the packing medium that promote mixing of the liquid transport medium and the analysis sample.

While the high stress in the material at the interface between the contact surface 34 and the landing area 40 will cause both the contact surface and the landing area to deform, it is preferable that the preponderance of the plastic deformation occurs in the material comprising the landing area. This embodiment is illustrated in detail in FIG. 1A, wherein the contact surface 34 of the compression body 32 is driven into the landing area 40 by tightening of the nut 30, causing the tube 16 to deform radially inwardly and form a lip 50 surrounding the opening 24. Deformation of the landing area also causes lip 50 to press against porous plug 20, trapping the plug within bore 14 and compressing it against the packing medium 18, thereby helping to maintain the hydraulic orientation of the medium and promote improved performance of the column. The lip 50 is advantageous because it compensates for variations in tolerance between the diameter of the tube bore 14 and the porous plug diameter. Looser tolerances between these parts are acceptable if, during tightening of the compression fitting 28, the tube 16 is deformed to positively engage the plug circumferentially and force it further into the bore. This ensures a tight seal between the plug and the tube that will not permit the packing medium to escape regardless of the tolerance stack up.

There are various ways to ensure that the plastic deformation of the metal to metal seal occurs primarily in the landing 40 and not in the contact surface 34. For example, the material from which the contact surface is made should have a higher yield strength than the material from which the landing area is made. To this end, it is advantageous to form the compression body as a separate piece from chrome nickel steel alloys, and the tube from lower strength stainless steels. The chrome nickel steel has a yield strength of twice the stainless and has the added advantage that it is non-galling.

Figure 2:
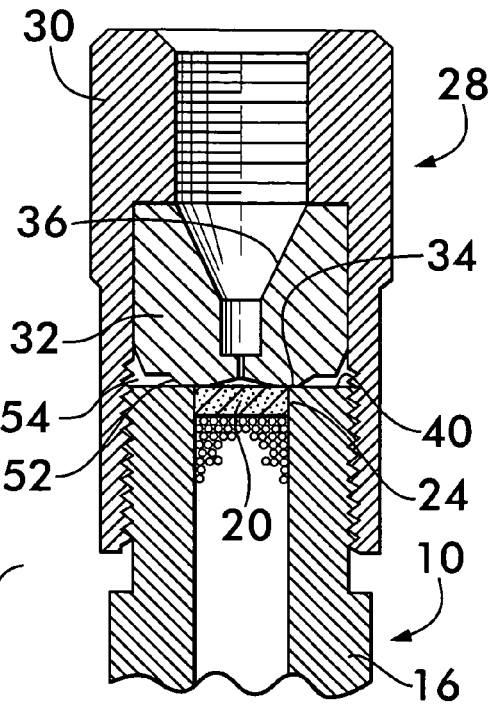
FIG. 2 is a longitudinal sectional view of an alternate embodiment of a column according to the invention.
Figure 2:
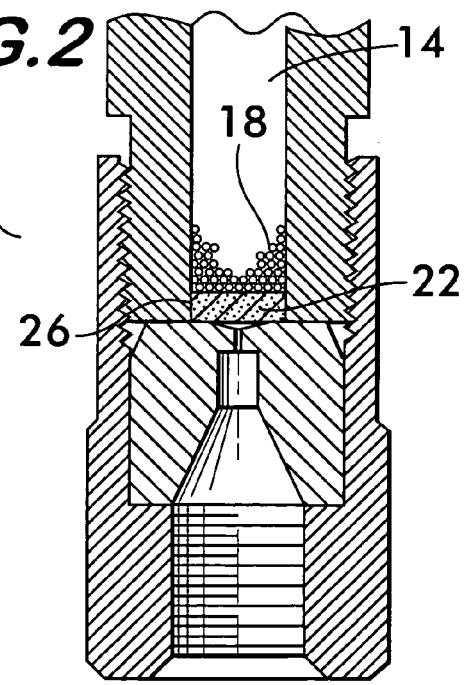

To further promote deformation of the tube over the compression body, the surface area of the contact surface 34 should be smaller than the surface area of the landing area 40. This will concentrate the contact pressure between the contact surface and the landing area over a smaller area of the tube, raising the stress and causing plastic deformation. The imbalance of surface areas may be achieved in various ways. As shown in FIGS. 1 and 1A, the chamfer 38 of the compression body 32 reduces the diameter of the compression body to less than the outer diameter of the tube 16 at the interface between the compression body and the tube. This concentrates the compressive force over a fraction of the landing area, that fraction preferably being close to and surrounding the inner diameter of the tube to promote the formation of lip 50 and the capture of the porous plug 20. In another embodiment, shown in FIG. 2, the contact surface 34 is formed on compression body 32 by a raised area or shoulder 52 that abuts the tube opening and projects outwardly from the end of the compression body. Shoulder 52 has a diameter less than the outer diameter of the tube. Both the chamfer 38 (FIGS. 1 and 1A) and the shoulder 52 (FIG. 2) concentrate the compression force between the compression body and the tube over a fraction of the landing area 40 and also allow a free space 54 at the end of the tube to accommodate bulk expansion of the material in reaction to the stress. Without such expansion space it would be very difficult to control the deformation of the tube, which is formed of material which, when constrained, is substantially incompressible. By way of example, tests have been performed on a column having an outer diameter of 0.315 inches, and inner diameter of 0.83 inches, the contact surface having a diameter of 0.123 inches. The example column was made from annealed stainless steel having a yield strength of about 30,000 psi. The compression fittings, having 40 threads/inch were torqued to about 55 in-lbs which produced a stress in the column of about 100,000 psi to effect the metal to metal seal.

The column embodiments thus far discussed are shown having ends that are identically configured with compression fittings 28 comprising threaded nuts 30 and separate compression bodies 32. It is understood however, that opposite ends of the column may have a different arrangement of parts and need not be identical.

Figure 3:
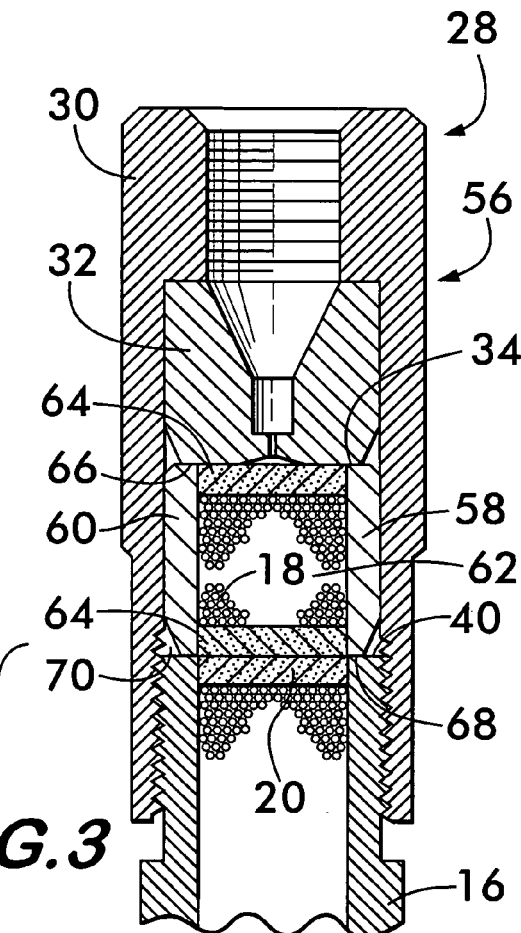
FIG. 3 is a longitudinal sectional view of another embodiment of a column according to the invention.
Figure 3:
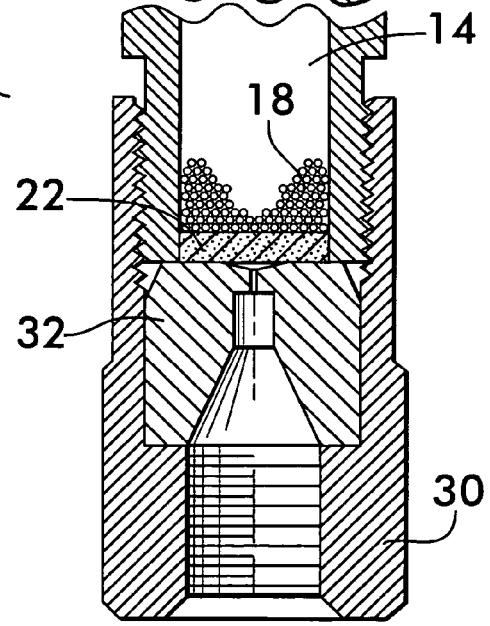

FIG. 3 shows another embodiment of a column 56 according to the invention. Column 56 comprises a tube 16 having a bore 14 in which packing medium 18 is contained. Porous plugs 20 and 22 are inserted within bore 14, preferably with an interference fit as described above. At the lower end of the tube 16 a compression body 32 engages the tube and a nut 30 engages both the tube and the compression body to force the compression body against the tube and form a metal to metal seal as previously described. At the other end of the column 56, a guard column 58 is positioned between the tube 16 and the compression body 32. Both the compression body and the guard column are captured by a threaded nut 30 that engages the tube. Guard column 58 comprises a second tube 60 having a bore 62 with openings at either end. Bore 62 receives packing medium 18. The packing medium is contained within the tube 60 by porous plugs 64 inserted into bore 62 at each open end. Similar to plugs 20 and 24, plugs 64 are preferably sintered stainless steel and engage tube 60 in an interference fit designed to contain the packing medium within the tube without the need for further sealing elements. As illustrated in the figure, guard columns are typically shorter than the column which they are attached to (tube 16) and serve to protect the column from contaminants and thereby increase its useful life.

Guard column 58 has a landing area 66 at one end that surrounds one of the guard column openings. Landing area 66 interfaces with the contact surface 34 of compression body 32. Tightening of the nut 30 forces the compression body against the guard column and forms a metal to metal seal between the landing area 66 and the contact surface 34, preferably by deforming the landing area as described above.

A contact surface 68 is positioned at the opposite end of the guard column 58. The contact surface is shown in this example as defined by a chamfer 70, but may also be formed by a raised shoulder as previously described. Contact surface 68 surrounds one of the openings in the guard column and engages the landing area 40 on tube 16. A metal to metal seal is formed between the contact surface 68 and the landing area 40 when compression fitting 28 is tightened. The contact surface 68 may be hardened, for example by heat treatment, so that it deforms the landing area 40 of tube 16 when compressed. It is preferable not to harden the entire tube 60 so that the compression body 32 will effectively deform the landing area 66 and form a fluid tight metal to metal seal.

What is claimed is:

1. A column for liquid chromatography, said column adapted to contain a packing medium, said column comprising:
    a chamber for receiving said packing medium;
    an opening in said chamber allowing liquid to pass therethrough;
    a porous plug blocking said opening for retaining said packing medium within said chamber;
    a landing area surrounding said opening;
    a compression fitting mounted on said chamber and having a contact surface engageable with said landing area;
    a duct extending through said compression fitting in fluid communication with said opening; and
    said compression fitting being adjustably movable to force said contact surface against said landing area thereby deforming one of said landing area and said contact surface to form a fluid tight seal between said compression fitting and said chamber.

2. A column according to claim 1, wherein said chamber comprises a tube having an axial bore therethrough, an end of said tube comprising said opening.

3. A column according to claim 1, wherein said landing area yieldably deforms.

4. A column according to claim 3, wherein said porous plug is positioned within said chamber, deformation of said landing area forming a lip that projects into said chamber and engages and captures said porous plug.

5. A column according to claim 1, wherein said contact surface has an area less than the area of said landing area.

6. A column according to claim 1, wherein said impression fitting includes a threaded nut and a compression body, said compression body being captured between said chamber and said nut, said contact surface comprising a raised shoulder positioned on an end of said compression body.

7. A column according to claim 1, wherein said impression fitting comprises a threaded nut and a compression body captured between said nut and said chamber, one end of said compression body having a chamfer, said chamfer surrounding said contact surface.

8. A column according to claim 1, further comprising:
    a second opening in said chamber allowing liquid to pass therethrough;
    a second chamber for receiving said packing medium;
    a third opening in said second chamber allowing liquid to pass therethrough, said third opening being in fluid communication with said second opening;
    a porous plug blocking said third opening for retaining said packing medium within said second chamber;
    a second landing area surrounding said third opening;
    a second contact surface surrounding said second opening and engageable with said second landing area, said compression fitting being adjustably movable to force said second contact surface against said second landing area thereby deforming one of said second contact surface and said second landing area to form a fluid tight seal between said chambers.

9. A column for liquid chromatography, said column adapted to contain a packing medium, said column comprising:
    a tube having an axial bore therethrough, said bore containing said packing medium;
    an opening positioned at one end of said tube;
    a landing area surrounding said opening;
    a porous plug positioned within said bore at said opening for retaining said packing medium within said tube;
    a compression fitting mounted on said one end of said tube, said compression fitting having a contact surface engageable with said landing area;
    a duct extending through said compression fitting in fluid communication with said opening; and
    said compression fitting being adjustably movable to force said contact surface against said landing area thereby deforming one of said landing area and said contact surface to form a fluid tight seal between said compression fitting and said tube.

10. A column according to claim 9, wherein said porous plug engages said bore with an interference fit.

11. A column according to claim 9, wherein said landing area yieldably deforms and forms a lip extending substantially radially inwardly of said bore, said lip engaging and capturing said porous plug within said bore.

12. A column according to claim 9, wherein said contact surface has an area less than the area of said landing area.

13. A column according to claim 9, wherein said compression fitting comprises a threaded nut and a compression body, said compression body being captured between said nut and said tube, said contact surface comprising a raised shoulder positioned on an end of said compression body.

14. A column according to claim 9, wherein said compression fitting comprises a threaded nut and a compression body captured between said nut and said tube, one end of said compression body being chamfered, said chamfer surrounding said contact surface.

15. A column according to claim 9, wherein said compression fitting is threadedly engaged with said tube, rotation of said compression fitting relatively to said tube adjustably moving said compression fitting and forcing said contact surface against said landing area.

16. A column according to claim 9, further comprising:
    a second opening positioned at an opposite end of said tube;
    a second porous plug positioned within said bore at said second opening for retaining said packing medium within said tube;
    a second landing area surrounding said second opening; and a second compression fitting mounted on said opposite end of said tube and having a second contact surface engageable with said second landing area, said second compression fitting being adjustably movable to force said second contact surface against said second landing area thereby deforming one of said second landing area and said second contact surface to form a fluid tight seal between said second compression fitting and said tube.

17. A column according to claim 9, further comprising:
a second opening positioned at an opposite end of said tube;
a second tube having an axial bore for receiving said packing medium;
a third opening positioned at one end of said second tube, said third opening being in fluid communication with said second opening;
a porous plug positioned within said bore at said third opening for retaining said packing medium within said second tube;
a second landing area surrounding said third opening;
a second contact surface surrounding said second opening and engageable with said second landing area, said compression fitting being adjustably movable to force said second contact surface against said second landing area thereby deforming one of said second contact surface and said second landing area to form a fluid tight seal between said tubes.

18. A column for liquid chromatography, said column comprising:
a tube having an axial bore therethrough, said bore containing a packing medium;
first and second porous plugs position within said bore at opposite ends of said tube, said porous plugs retaining said packing medium within said bore;
first and second landing areas positioned at opposite ends of said tube and surrounding said bore;
first and second compression bodies positioned at opposite ends of said bore, each said compression body having a contact surface engageable with one of said landing areas, each said compression body having a duct therethrough in fluid communication with said bore;
first and second threaded nuts mounted on opposite ends of said tube and engageable, respectively, with said first and second compression bodies, said threaded nuts being adjustably movable to force said contact surfaces of said compression bodies against said landing areas of said tube thereby deforming said landing areas to form a fluid tight seal between said compression bodies and said tube.

19. A column according to claim 18, wherein each of said contact surfaces comprises a raised shoulder positioned on an end of each of said compression bodies.

20. A column according to claim 18, wherein each of said compression bodies has a chamfer positioned at one end defining said contact surface.

21. A column according to claim 18, wherein said first and second landing areas yieldably deform and form respective first and second lips that extend inwardly of said bore at opposite ends of said tube, said first and second lips engaging and capturing, respectively, said first and second porous plugs within said bore.

* * * * *